US008399238B2

(12) United States Patent
Tournade et al.

(10) Patent No.: US 8,399,238 B2
(45) Date of Patent: Mar. 19, 2013

(54) SHELF-STABLE PRODUCT WITH LIVING MICRO-ORGANISMS

(75) Inventors: Sylvie Tournade, Caen (FR); Frederic Aymes, Montevrain (FR); Roberto Reniero, Bagno Aripoli (IT)

(73) Assignee: Nestec S.A., Vevey (CH)

( * ) Notice: Subject to any disclaimer, the term of this patent is extended or adjusted under 35 U.S.C. 154(b) by 1139 days.

(21) Appl. No.: 10/598,908

(22) PCT Filed: Mar. 23, 2005

(86) PCT No.: PCT/EP2005/003089
§ 371 (c)(1),
(2), (4) Date: Jul. 25, 2007

(87) PCT Pub. No.: WO2005/089560
PCT Pub. Date: Sep. 29, 2005

(65) Prior Publication Data
US 2007/0280909 A1 Dec. 6, 2007

(30) Foreign Application Priority Data

Mar. 24, 2004 (EP) .................................... 04007040

(51) Int. Cl.
*C12N 1/12* (2006.01)
(52) U.S. Cl. .................. 435/252.1; 435/243; 435/253.4; 435/260; 424/93.44; 424/93.45; 426/61
(58) Field of Classification Search .................. None
See application file for complete search history.

(56) References Cited

U.S. PATENT DOCUMENTS

| 4,886,664 A | 12/1989 | Jung et al. |
| 4,956,186 A | 9/1990 | Streiff et al. |
| 5,071,763 A | 12/1991 | Somkuti et al. |
| 5,382,438 A * | 1/1995 | Hottinger et al. ............... 426/43 |
| 6,606,822 B2 | 8/2003 | Bonfiglio |
| 6,875,601 B1 | 4/2005 | Benbadis et al. |
| 7,780,970 B2 * | 8/2010 | Schlothauer et al. ...... 424/282.1 |
| 2003/0031754 A1 | 2/2003 | Lange |
| 2003/0060496 A1 | 3/2003 | Meritt et al. |
| 2004/0191233 A1 | 9/2004 | O'Sullivan |

FOREIGN PATENT DOCUMENTS

| EP | 0092183 | 1/1989 |
| EP | 0199535 | 1/1992 |
| EP | 0402450 | 5/1994 |
| EP | 0652285 | 5/1995 |
| EP | 0667106 A1 | 8/1995 |
| EP | 0508701 | 7/1996 |
| EP | 0965643 | 12/1999 |
| EP | 1384483 | 1/2004 |
| EP | 1345613 | 4/2008 |
| FR | 2224096 | 10/1974 |
| GB | 2252228 | 8/1992 |
| WO | WO99/61627 | 12/1999 |
| WO | WO00/53200 | 9/2000 |
| WO | WO 00/53202 | * 9/2000 |
| WO | WO01/88150 | 11/2001 |
| WO | WO02/15702 | 2/2002 |
| WO | WO02/43649 | 6/2002 |
| WO | WO2005/017095 | 2/2005 |

OTHER PUBLICATIONS

Kailasapathy K., Current Issue Intest. Microbiol., 2002, vol. 3, p. 39-48.*
Fleming et al., Journal of Food Science 1983, vol. 48, p. 975-981.*
Abstract XP-002292992, Effects of Water and Salt Level on Rheological Properties of Ayran, A Turkish Yoghurt Drink, Application No. 2004-00-p0572.
Abstract XP-002292994, Liquid Yogurt Drink With Specified pH—Containing Bifido-Bacteria and Citrate Salt for Good Stability, Application No. 1989-035915.
Abstract XP-002292993, Sugar Profiles of Cultured Dairy Products in the UK, Application No. 2000-00-p1138.
Hartke et al. "Survival of Enterococcus faecalis in an Oligotrophic Microcosm: Changes in Morphology, Development of General Stress Resistance, and Analysis of Protein Synthesis," Applied and Environmental Microbiology, Nov. 1998, p. 4238-4245.
Chou et al. "Growth of bifidobacteria in soymilk and their survival in the fermented soymilk drink during storage," International Journal of Food Microbiology, 56 (2000) 113-121.
Tamime "Probiotic Dairy Products," Blackwell Publishing 2005.
CAST(Council for Agricultural Science and Technology) "Probiotics: Their Potential to Impact Human Health," No. 36, Oct. 2007, p. 1-19.
Salminen et al. "The Efficacy and Safety of Probiotic Lactobacillus rhamnosus GG on Prolonged, Noninfectious Diarrhea in HIV Patients on Antiretroviral Therapy: A Randomized, Placebo-Controlled, Crossover Study," HIV Clinical Trials, 5/4, Jul.-Aug. 2004, p. 183-191.
Declaration of Kalle (Kaarle) Leporanta, dated Nov. 24, 2008.
Reid et al. "Probiotics: Some evidence of their effectiveness," Canadian Family Physician, vol. 51, Nov. 2005, p. 1487-1493.
Catroux et al. "Trends in rhizobial inoculant production and use," Plant and Soil, 230, 2001, p. 21-30.
The McDougall Newsletter "Beneficial Bowel Bacteria—Our Neglected Friends," vol. 4, No. 8, Aug. 2005.
MINTEL Global New Products Database Extracts (6 pages).

*Primary Examiner* — Kade Ariani
(74) *Attorney, Agent, or Firm* — K&L Gates LLP

(57) ABSTRACT

The present invention relates to shelf-stable liquid products, for example diary products, comprising micro-organisms, especially probiotics. The micro-organisms are able to survive for several months at room temperature basically due to their inability to metabolise nutrients contained in the liquid product. The invention further relates to a method for manufacturing the liquid product according to the invention.

12 Claims, 2 Drawing Sheets

SHELF-STABLE PRODUCT WITH LIVING MICRO-ORGANISMS

The present invention relates to a liquid product, which is water- or milk-based and which comprises living micro-organisms, and which is basically shelf stable. The present invention further relates to a method for preparing a liquid, water- or milk-based delivery system for micro-organisms, and a method for providing to a consumer living micro-organisms in a water- or milk based liquid.

The bacterial population of the human or animal gastro-intestinal tract constitutes an enormously complex ecosystem that includes many types of microorganisms. There are more than 400 different species of bacteria in an individual's microbiota (=bacterial micro-flora), the total population of which is approximately $10^{14}$ cells. From the stomach to the colon the number of bacteria increases throughout the gastrointestinal tract. The highest bacterial counts are found in the colon with up to $10^{11}$ colony forming units (cfu) per ml gut content.

Depending of the kind of a specific bacterium that is part of the microbiota it may live in a parasitic, commensal or symbiotic relationship with its host. Many beneficial effects may be exerted by symbiotic bacteria, for example prevention of constipation and/or diarrhea, enhancement of mineral absorption, protection from infection, prevention of cancer, immunomodulation and others. Micro-organisms that have a beneficial effect on their host, including bacteria, are generally referred to as probiotic micro-organisms or probiotics.

In order to provide to a consumer the beneficial functionalities of probiotics, huge efforts have been made to prepare probiotics in sufficient quantity in an orally consumable form. These efforts, however, were repeatedly confronted with several technical problems linked to the production and stabilisation of probiotic preparations.

For example, the fact that many probiotic bacteria possess an anaerobic metabolism imposes specific technical requirements on all process and product levels between a starting culture and a consumable product suitable to deliver said bacterium in sufficiently high concentration to a human or animal.

Actually, the mere fact that living bacteria are metabolically active—even at chilled temperatures—imposes problems: ingestible carriers of probiotics often sustain degradation by the bacterial activity, which may render the carrier completely unpalatable.

It is another pertinent problem to warrant that sufficient amounts of probiotic arrive in a living state in the small and large intestines. As a matter of fact, the acidity of the stomach as well as the exposure to bile acids drastically reduce survival of bacteria during the passage of the gastro-intestinal tract.

In the prior art many possibilities for providing probiotic bacteria are reported. A generally applied approach to obtain a stable preparation of probiotics comprises the steps of conducting a fermentation to obtain high cfu of bacteria, adding a carrier or protective material, such as carbohydrates or milk powder, and, drying the mixture, for example by freeze-drying. In this way, a bacterial preparation with low Aw and prolonged shelf life may be obtained. A disadvantage of a hot drying or a freeze-drying process as applied according to this principle is, however, that significant losses of living bacteria must be accounted for. Furthermore, only dried products are obtained according to this kind of procedure. It would be advantageous to have more convenient forms of consumption.

Another way of delivering a probiotic is the preparation of a material, which was fermented by the probiotic. This is the case, for example, with yoghurts that were obtained from fermenting milk with micro-organisms. The advantage of these products is that they are relatively stable when chilled, due to the low pH of the product after fermentation. However, the acid produced by the fermenting activity of the probiotic does not correspond to every consumer's taste. In addition, these products still have to be chilled.

Similarly, "sweet acidophilus milks" which are commercially available have to be chilled in order to prevent deterioration and fermentation of the product (see EP 0 154 614B1, Col. 2, lines 27-33). This holds true even though the product itself has not been fermented.

EP 0 154 614 discloses a method of cultivating, in milk, organisms that have a slow growth capacity. Basically, a bulk starter is prepared together with milk, which is kept at optimum growth conditions until a pH of 4.5-5 is reached. Thereafter the bulk starter is added to a process milk batch and cultivated therein, again at optimum growth conditions, until a bacterial content of $10^8$ cfu per ml is obtained. This is an acidified product and thus has the same disadvantages as reported above.

In view of the prior art it is an objective to provide other means or another delivery system for probiotic micro-organisms.

It is another objective to find a way of providing probiotics without the losses during a drying step.

Furthermore, it is an objective to provide viable probiotics while avoiding the costs and energy expenditures associated with the cooling or chilling of a probiotic preparation.

In addition, it is an objective of the present invention to provide probiotics in the form of a product that has a prolonged shelf life and a convenient way of being consumed.

Remarkably, it has been found that probiotic micro-organisms may be kept stable in a water- or milk-based liquid at room temperature for a prolonged time, such as several months. This surprising finding could be obtained, for example, when the probiotics were provided in a liquid that does not contain carbohydrates that may be digested by the micro-organism.

Accordingly, the present invention provides, in a first aspect a liquid product, which is water- or milk-based and which comprises living micro-organisms, characterised in that the liquid product has a shelf-life of at least 1 month at 10°, during which the pH of the product decreases less than 2 points and/or the amount of living bacteria decreases less than 2 log-units.

In a further aspect, the present invention provides a method for manufacturing a liquid, water- or milk-based delivery system for micro-organisms, which is shelf stable for at least 1 month at 10° C., the method comprising the steps of fermenting a medium to obtain a biomass of living micro-organisms, and adding the biomass to a water-based liquid which is free of carbohydrates that can be metabolised by the micro-organism.

In another aspect, the present invention provides a method for providing to a consumer living micro-organisms in a water- or milk-based liquid, the method comprising the step of administering to a consumer the product according to the invention.

In still another aspect, the present invention provides the use of micro-organisms in water- or milk based liquid, shelf-stable products.

In another aspect, the present invention provides a liquid product, providing benefits of living probiotics, whereby the product can be stored at temperatures above 10° C. for at least one month.

In yet another aspect the present invention provides a method for providing to an individual benefits of living probiotics, the method comprising the step of providing to the individual the product according to the invention.

In still a further aspect, the present invention provides a method for distributing living micro-organisms in a consumable form, the method comprising the steps of distributing the product according to the invention.

In the figures.

Figure 1:
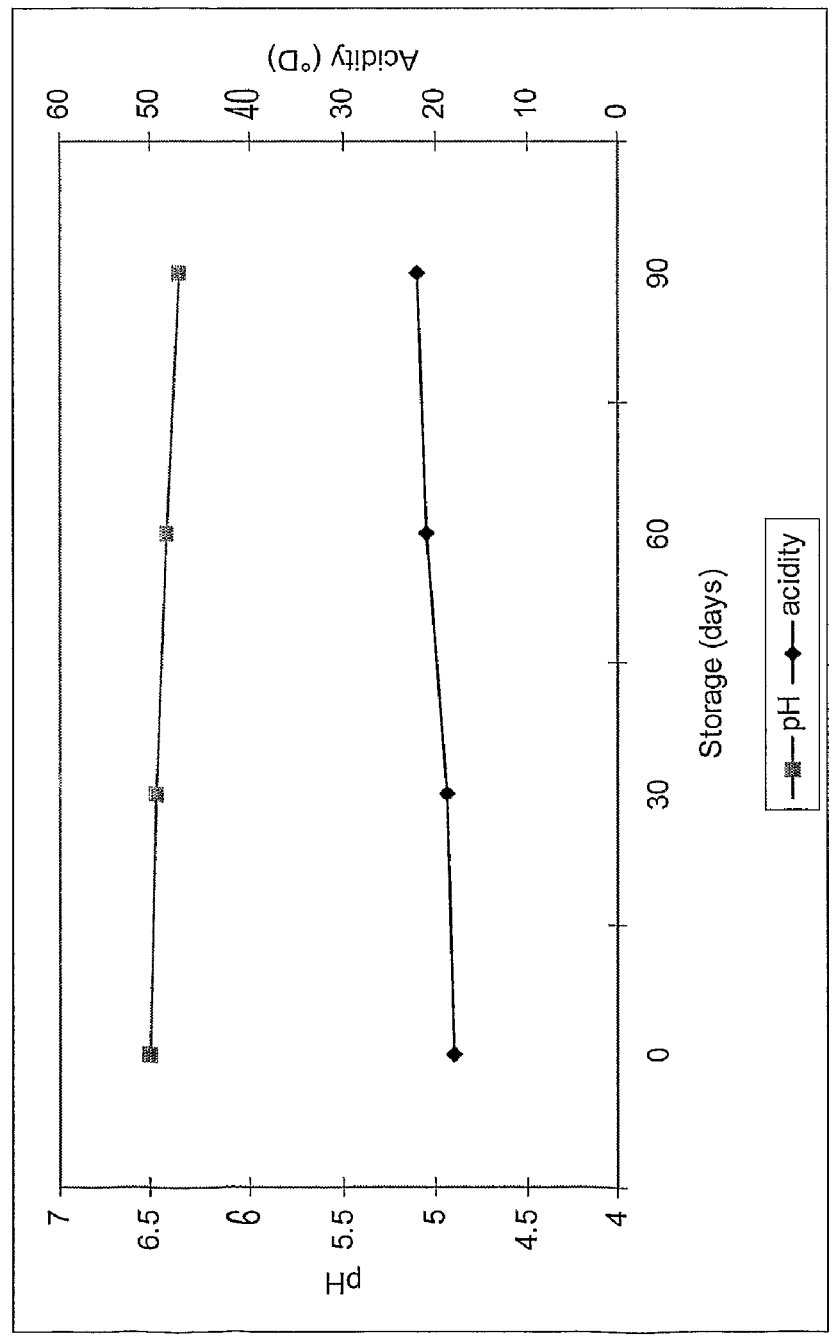
FIG. 1 shows pH and acidity in ° Dornic over two months a product according to the present invention inoculated with micro-organisms at $2\text{-}5\times10^7$ cfu/ml.

Within the context of this specification the word "comprises" is taken to mean "includes, among other things". It is not intended to be construed as "consists of only".

In the context of the present invention, the products according to the invention comprising living micro-organisms may also be referred to as delivery systems for said micro-organisms.

The term "water- or milk-based liquid" refers to any liquid, which is not hydrophobic. For example, the term excludes lipid- or oil based liquids. The term includes, however, emulsion-type of liquids containing lipid droplets in a hydrophilic base, for example.

Preferably, the liquid product according to the invention has a Brookfield viscosity of below 200 Pa s$^{-1}$. More preferably, the liquid product according to the invention has a Brookfield viscosity of below 100 Pa s$^{-1}$, most preferably, the liquid product has a Brookfield viscosity of below 20 Pa s$^{-1}$. The Brookfield viscosity is established at a shear rate of 5 RPM and at a temperature of 8° C. These values were established with a Brookfield DV-II+ viscometer.

The term "shelf-stable" generally means that the product does not need to be chilled at 8° C. or below, but can be stocked in an un-chilled shelf of a super-market. The temperature in a super market is usually in the range between 16-25° C.

For the purpose of the present invention, the "shelf life" of a product is taken to start at the moment on which the manufacture of the product is completed, that is, after filling and sealing of the product. For simplicity and for giving a clear moment, the further time that it may take until the product is on the shelf in a super market is not taken into consideration for the starting point of the "shelf life" according to the present invention. This is due to the high variability of the time between manufacture and appearance in the super market, which in practice may depend on many, inconstant factors.

In an embodiment, the products of the present invention are characterised in that they comprise milk proteins, lactose and/or other milk or milk derived solids.

In particular, milk solids include dairy products or products containing ingredients that are derived from milk, for example milk protein, such as whey proteins, casein protein, milk carbohydrates, such as lactose, or milk lipids, such as cream, for example. Preferably, the product according to the present invention comprises milk protein.

Accordingly, the product may be a whole, skimmed, or half-skimmed milk, buttermilk, or a reconstituted milk, based on a milk powder, for example.

Preferably, the liquid product is a milk that was sterilised, for example by ultra heat treatment (UHT). Preferably, the products are shelf-stable, liquid dairy products.

Alternatively, the products according to the present invention may be a syrup, a soft drink, a carbonated soft drink, a tea, such as a cold tea, a juice, such as an apple, orange or generally fruit juice, for example.

The products may also be a soy-based product. For example, it may be a soy-milk or a soy-drink. For example, the liquid product may be a soy-based replacement for milk. The soy-based product may be free of lactose.

The product according to the present invention preferably has a water activity of 0.4 or above, more preferably 0.6 or above, even more preferably 0.7 or above. For example, the product according to the invention has a water activity of 0.8 or above.

Preferably, the product according to the present is a non-fermented product.

However, the product according to the present invention may be envisaged to be a fermented product, which was obtained, for example, by fermenting a medium, heat treating or pasteurising the medium to reduce bacterial load, and, at the same time, kill the fermenting bacteria. Then the fermented, optionally pasteurised product could be supplemented with a micro-organism according to the present invention, which will not further grow on the fermented medium. For example, the product may be a yoghurt, which is heat-treated and to which micro-organisms which are not able to grow on the fermented, heat-treated product are added, in order to obtain a product which fulfills the features of the present invention. Accordingly, the product according to the present invention may be a stirred or set yoghurt, which is natural or which has additional flavours or ingredients, for example fruits. The product according to the invention could also be a shelf stable fresh cheese.

The term "log unit" refers to the logarithm on the base of ten. Therefore, a decrease of one log-unit cfu refers to, for example a decrease from $10^9$ to $10^8$ cfu. In other words, a decrease of one log unit means a decrease to 10% of the starting value of 100%, for example.

A decrease in one pH point may be illustrated at the example of a pH decrease of from 7.0 to 6.0, or from 6.5 to 5.5. A decrease in 2 pH points may be a decrease from pH 6.7 to pH 4.7, for example.

In an embodiment, the products of the present invention are free of carbohydrates that can be metabolised by the micro-organisms. For example, if the liquid product comprises lactose, the micro-organism is preferably a bacterium that cannot metabolise lactose.

Therefore, in a further embodiment of the present invention, the micro-organisms cannot use lactose as a nutrient. Examples for micro-organisms that cannot use lactose are *Lactobacillus paracasei* (CNCM I-2116), or *Lactobacillus rhamnosus* (ATCC53103).

According to another example according to the present invention, the micro-organism cannot use sucrose as a nutrient. *Lactobacillus delbruecki* subsp *bulgaricus* (ATCC 11842), and *Lactobacillus helveticus* (ATCC15009) are strains that cannot use sucrose as a substrate.

Alternatively, the product of the present invention may be free of another carbohydrate source that could be metabolised by the micro-organism.

For illustrating the principle of the present invention it is theoretically assumed that if any of the products of the present invention is free of sucrose, but contains other carbohydrates, the micro-organism comprised in the product may be able to metabolise or use as a macro-nutrient only the missing carbohydrates, such as sucrose, for example.

The product according to the present invention is preferably free of one or more of the carbohydrates selected from the group consisting of fructose, glucose and sucrose. Preferably, it is free of glucose and/or fructose, more preferably they are free of sucrose.

For the purpose of the present invention, the term "free of a carbohydrate", for example "free of sucrose", refers to liquid products in which the carbohydrate is present in amounts smaller than 0.2 g per 100 ml of the liquid product.

Preferably, the carbohydrate source is present in amounts smaller than 0.1 g/100 ml, more preferably less than 0.05 g/100 ml, most preferably less than 0.01 g/100 ml.

The product may be originally free of potentially fermentable carbohydrates, due to the selection of its ingredients. Alternatively, all potentially fermentable carbohydrates may have been removed from the product or its ingredients.

Accordingly, if the micro-organism is capable of using sucrose, fructose and glucose, the liquid product is preferably free of any of these three carbohydrates.

Preferably, the micro-organisms is naturally incapable of using carbohydrates that are present in the liquid product. For example, it may be a strain which naturally cannot use lactose. For example, it can be a natural mutant. Alternatively, the micro-organism may be genetically engineered to be unable to grow on specific carbohydrates.

Preferably, the micro-organism is a bacterium. More preferably, it is a lactic acid bacterium.

In a preferred embodiment, the micro-organism is a probiotic.

In an embodiment of the present invention, the micro-organism is a strain selected from the group of genera consisting of *Lactobacillus, Bifidobacterium, Streptococcus, Lactococcus, Enteroccus* and mixtures of these.

Preferably, the micro-organism is a *Lactobacillus*-strain. More preferably it is selected from the group consisting of *L. casei, L. paracasei, L. acidophilus, L. plantarum*, and mixtures of these. Preferably, the micro-organism is a *L. paracasei*-strain, for example, the micro-organism is *Lactobacillus paracasei* (CNCM I-2116).

Preferably, the liquid product according to the present invention comprises at least $10^4$ cfu of the micro-organism per ml at the beginning of shelf life. More preferably, at least $10^5$, even more preferably, at least $10^7$, most preferably at least $10^8$ cfu/ml. For example, the liquid product comprises at least $10^6$ cfu/ml.

Preferably, the liquid product according to the present invention contains $10^5$-$10^9$, more preferably $10^6$-$10^8$ cfu of the micro-organism per ml during the whole shelf life as defined according to the invention.

In an embodiment of any of the liquid product according to the present invention, the liquid products has shelf life of at least 1 month at 20° C. during which the product experiences a decrease in pH of less than 2 points and during which the loss of living micro-organisms is less than 2 log-units. Preferably, the decrease in pH is less than 1 unit, more preferably less than 0.5 unit.

The liquid product according to the present invention preferably has a shelf-life of at least 2 months at 20° C. during which the pH of the products decreases less than 2 points and the amount of living micro-organisms decreases less than 2 log units. Preferably, the decrease in pH is less than 1 unit, more preferably less than 0.5 unit.

Preferably, the liquid product according to the present invention has a shelf life of at least 2 months at 20° C. during which the pH decreases less than 2 points and the amount of living micro-organisms decreases less than 1.5 log units. Preferably, the pH decreases less than 1 log unit, more preferably less than 0.5 unit.

Preferably, the liquid product according to the invention has a shelf live of at least 2 months at 20° C. during which the pH decreases less than 1 point and the amount of living micro-organisms decreases less than 2 log units. Preferably, the amount of living micro-organisms decreases less than 1 log unit, more preferably less than 0.5 log units.

Preferably, the liquid product according to the invention has a shelf live of at least 2 months at 20° C. during which the pH decreases less than 0.7 point and the amount of living micro-organisms decreases less than 2 log units. Preferably, the amount of living micro-organisms decreases less than 1 log unit, more preferably less than 0.5 log units.

For example, the product may have a shelf life of at least 2 months at 20° C. during which the pH decreases less than 0.7 points and the amount of living bacteria decreases less than 1, preferably less than 0.5, more preferably less than 0.3 log units.

Preferably, the liquid product according to the present invention has shelf life of at least 1 month at 25° C. during which the product experiences a decrease in pH of less than 2 points and during which the loss of living micro-organisms is less than 2 log-units. Preferably, the decrease in pH is less than 1 unit, more preferably less than 0.7 unit.

The liquid product according to the present invention preferably has a shelf-life of at least 2 months at 25° C. during which the pH of the products decreases less than 2 points and the amount of living micro-organisms decreases less than 2 log units. Preferably, the decrease in pH is less than 1 unit, more preferably less than 0.5 unit.

Preferably, the liquid product according to the present invention has a shelf life of at least 2 months at 25° C. during which the pH decreases less than 2 points and the amount of living micro-organisms decreases less than 1.5 log units. Preferably, the pH decreases less than 1 log unit, more preferably less than 0.5 unit.

Preferably, the liquid product according to the invention has a shelf live of at least 2 months at 25° C. during which the pH decreases less than 1 point and the amount of living micro-organisms decreases less than 2 log units. Preferably, the amount of living micro-organisms decreases less than 1 log unit, more preferably less than 0.5 log units.

Preferably, the liquid product according to the invention has a shelf live of at least 2 months at 25° C. during which the pH decreases less than 0.7 point and the amount of living micro-organisms decreases less than 2 log units. Preferably, the amount of living micro-organisms decreases less than 1 log unit, more preferably less than 0.5 log units.

Preferably, the product may have a shelf life of at least 2 months at 25° C. during which the pH decreases less than 0.7 points and the amount of living bacteria decreases less than 1, preferably less than 0.5, more preferably less than 0.3 log units.

Preferably, all the above-indicated parameters of shelf life of the product according to the present invention, as defined by storage temperature (10, 20, or 25° C.), decrease in pH (2, 1, 0.5, 0.3 points) and cfu (2, 1.5, 1, 0.5, 0.3 log units) may be obtained for a shelf-life of as much as 3 months or more.

The product may have any pH in the range of 3.4-8, preferably 4-7.5, most preferably 6-7, as long as the specific pH in this range remains stable during shelf life as defined according to the present invention.

For example, the pH of the product according to the present invention remains in the range of 6-7 during a shelf life of 2 months at 20° C.

In an embodiment, the pH of liquid product according to the present invention, before shelf life, is 3 or above. More preferably, the pH is 4 or above, even more preferably 5 or above, still more preferably, it is 6 or above. For example, the pH of the product is 5.5 or above. Most preferably, the pH of the product at the beginning of shelf life is in the range of 6.1-7.8.

In an embodiment of the method for manufacturing the step of fermenting a medium is conducted for at least 7 hours at above 30° C., more preferably at least 8 hours above 35° C., for example at 37° C.

Optionally, the method for manufacturing the liquid, water- or milk based delivery system for micro-organisms, the method may further comprise the step of separating the biomass from the fermented medium and/or, as a further option, washing the biomass, before adding to the water- or milk based liquid. According to an additional option, the biomass may be frozen, dried or freeze-dried before adding it to the water- or milk based liquid.

In the method for providing to a consumer living micro-organisms, the consumer preferably is in need or wants to consume the living micro-organisms, and the micro-organisms are administered in sufficient amounts. Sufficient amounts usually means that at least $10^5$-$10^8$, preferably $10^6$-$10^7$ living micro-organisms are administered per serving. Preferably, at least one serving is consumed per day.

An aspect of the present invention provides liquid products or a method for providing benefits of living probiotics. There are many known benefits of living micro-organisms and many more may be discovered in the future. Examples of such benefits may are relieving gut pain, providing gut comfort, providing general well-being, increasing mineral absorption, preventing or reducing constipation and/or diarrhoea, protecting from infection, preventing infection, immunomodulation, increasing immune responses against pathogens or parasites, and prevention of cancer. One or more micro-organisms may be selected and combined or mixed in a single preparation to alleviate one or more of these exemplary benefits.

Preferably, the product providing benefits of living probiotics may be stored at temperatures above 15° C. for at least 2 months. The storage time starts with the shelf life as defined above. More preferably, the product providing benefits of probiotics may be stored at temperatures and for time periods corresponding to those according to the other products according to the present invention. For example, the product may be stored at temperatures up to or above 25° C. for up to 3 months or more.

According to a further aspect, the present invention provides a method for distributing living micro-organisms in a consumable form. Preferably, the distribution corresponds to the distribution of shelf stable products. Shelf-stable and chilled products have usually different distribution patterns, in that chilled distribution channels require chilling at usually 6° C. or below during storage, transport and subsequent shelf life in a super market, for example. According to the present invention, the distribution, comprising transport, and optionally, storage in a store-house and/or in the shelf of a supermarket, may be performed at temperatures above 10° C., preferably at temperatures in the range of 10° C.-25° C., more preferably at temperatures between 14-20° C. This way of distributing living micro-organisms in a consumable form entails the advantage of lower energy expenditures during distribution, because basically chilling is necessary. Preferably, the living micro-organisms in consumable form correspond to the liquid product according to the invention.

EXAMPLE

A shelf stable, milk-based liquid comprising a probiotic strain was prepared according to the following procedure.
Material and Methods As a probiotic micro-organism, *Lactobacillus paracasei* (CNCM I-2116) was chosen. This strain is β-galactosidase-deficient and cannot, therefore, use lactose as a substrate of carbohydrates.

The experiment was independently conducted with a frozen concentrate as well as a starter preparation.

For the starter preparation the following medium was used:
1% yeast extract
2% glucose
1% calcium carbonate
0.05% manganese sulfate
95.05% water The medium was heat treated at 95° C. for 30 min and then cooled at 4° C. (not longer than 24 hours) or at 37° C. for immediate inoculation.

Inoculation was carried out with 0.05% by weight of a partly defrosted can of a frozen concentrate of the selected strain, which is characterised by 1-2×$10^{10}$ cfu of bacteria per gram of concentrate.

Fermentation was carried out at 37° C. during 11 hours under stirring conditions, followed by cooling at 4° C.

At the end of fermentation, a starter culture having a pH of 4.6 and containing $10^9$ cfu of *L. paracasei* per ml of fermented medium was obtained.

UHT half-skimmed milk was purchased in a supermarket. It was completed with a sweetener (0.01% by weight of sucralose) in order to give a sweet taste to the liquid product. Sucralose was added in the form of a sterile solution prepared by filtration: 5 g of sucralose were dissolved into 95 g of water. This 5% sucralose solution was sterilised by filtration with vacuum driven disposable filter system (membrane diameter 0.22 μm. From this sterile solution, 20 g (20 ml) were removed and added into 980 g of UHT purchased milk. The UHT-milk so obtained was thus free of any carbohydrate that could be metabolised by CNCM I-2116.

The milk was then inoculated with the strain so as to obtain a starting concentration of 2-5×$10^7$ cfu of CNCM I-2116 per ml.

In parallel, the same strain was added to another sample of half-skimmed milk directly in the form of the frozen concentrate discussed above, to obtain the same starting concentration of 2-5×$10^7$ cfu of CNCM I-2116 per ml.

The milks inoculated with the starter preparation and the frozen concentrate, respectively, was then mixed well before filling into sterile glass bottles.

Products were then stored for 2 months at 25° C. and analysed along the storage.

Analysis included measurements of pH, Dornic acidity and cell-counts (cfu).

For establishing cell counts of CNCM I-2116, the standard MRS medium (Man-Rogosa-Sharpe) for plating of lactobacilli was used. Before each cell-count, the milk bottle on storage was mixed well and 1 ml was taken to carry out the analysis. Appropriate dilutions were carried out on a diluent containing 1.5% tryptone, 0.85% NaCl and 0.01% of an anti-foaming agent. One ml portions of the dilution were mixed with the MRS agar in a Petri-dish.

Plates were examined after anaerobic incubation at 37° C. for 48 hours and the number of colony forming units per ml were calculated.

Results

Cfu-losses of CNCM I-2116 in UHT skimmed and half-skimmed milk, when stored at 25° C. remained, below 0.3 log and reached final value of $10^7$ cfu/ml after a shelf life of two months. In the same period, pH decreased from 6.50-6.40 to a final level of 6.30. The Dornic acidity increased very slightly along the storage at 25° C. from 18° D to 21 to a final level below 25° D.

FIG. 1 shows pH-development (square-symbols) and Dornic Degree (rhombus-symbols) development in the course of the storage period.

The Dornic acidity is a very sensitive value, which theoretically may change during shelf life even at constant pH. Even though this value has not the same importance as pH for the purpose of the present invention, the acidity values are of the shelf stable product are indicated for illustration of the stability of the product during a prolonged shelf life at 25° C.

Figure 2:
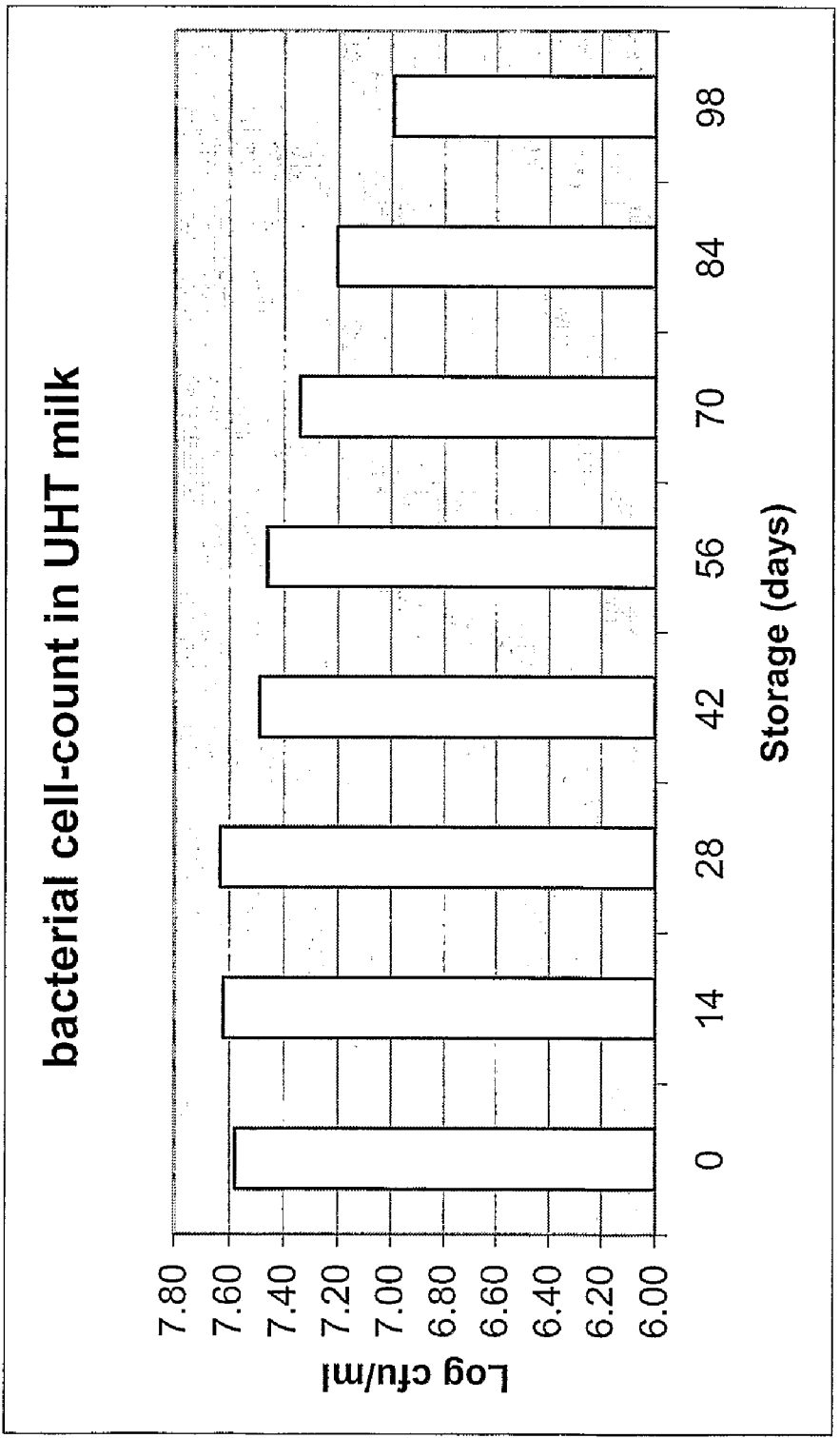
FIG. 2 shows cfu losses of bacteria stored at 25° C. in a liquid product according to the present invention over a period of 98 days.

FIG. 2 shows the decrease in log cfu/ml over a storage time of 98 days at 25° C. As can be seen, the mortality of bacteria remains very low during the first 70 days, resulting in a loss of cfu of less than 0.2 log.

The experiment surprisingly showed that bacterial preparations can be kept in a liquid, such as a milk, in a shelf-stable way, such as at 25° C. for two months without substantial loss of cell counts and without substantial decrease in pH. This makes the water- or milk based liquid a valuable, easy-to-handle delivery system or carrier for probiotic micro-organisms, which are unable to metabolise carbohydrates contained in the water- or milk based liquid.

The invention claimed is:

1. A water- or milk-based liquid product comprising living microorganisms selected from the group consisting of *Bifidobacterium, Streptococcus, Lactococcus, Enterococcus* and mixtures of same, the liquid product having a pH from about 4 to about 7.5 and a shelf-life of at least 1 month at 20° C., during which period the liquid product experiences a decrease in pH of less than 2 points and an amount of living microorganisms decreases less than 2 log-units, and wherein the liquid product is free of carbohydrates that can be metabolised by the microorganisms.

2. The product according to claim 1, comprising a component selected from the group consisting of milk proteins, lactose, milk and milk-derived solids.

3. The product according to claim 1, wherein the microorganisms are not capable of using lactose as a nutrient.

4. The product according to claim 1, wherein the microorganisms are probiotics.

5. The liquid product according to claim 1, wherein the liquid product is a non-fermented product.

6. The liquid product according to claim 1, comprising lactose, and the microorganisms are incapable of using lactose as a nutrient.

7. The liquid product according to claim 1, comprising sucrose, and the microorganisms are incapable of using sucrose as a nutrient.

8. The liquid product according to claim 1, wherein the decrease in pH is less than 0.5 units during the shelf-life.

9. The liquid product according to claim 1, wherein the amount of living microorganisms decreases less than 0.5 log units during the shelf-life.

10. The liquid product according to claim 1, wherein the amount of living microorganisms decreases less than 0.3 log units during the shelf-life.

11. The liquid product according to claim 1, wherein the amount of living microorganisms is between $10^6$ and $10^8$ cfu/ml during the entirety of the shelf life.

12. The liquid product according to claim 1, wherein the pH of the liquid product is in the range of 6-7 during the entirety of the shelf life.

* * * * *